Figure 1:
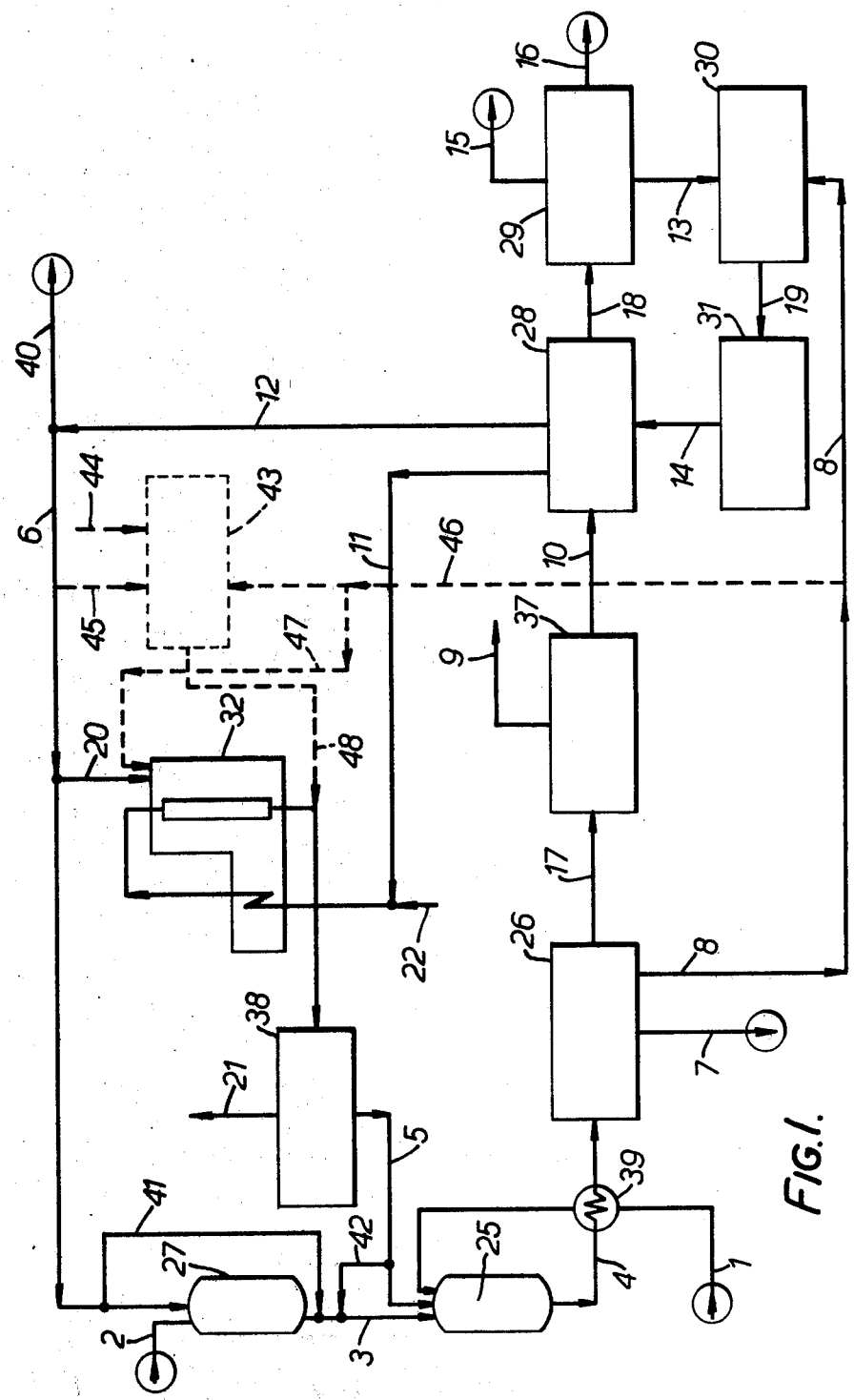

United States Patent [19]

Fowler

[11] 4,115,467
[45] Sep. 19, 1978

[54] HYDROCARBON CONVERSION PROCESS

[75] Inventor: Ray Fowler, Amersham, England

[73] Assignee: Davy Powergas Limited, London, England

[21] Appl. No.: 714,260

[22] Filed: Aug. 13, 1976

[30] Foreign Application Priority Data

Aug. 14, 1975 [GB] United Kingdom ............... 33928/75

[51] Int. Cl.² ............................................. C07C 11/04
[52] U.S. Cl. .................................. 260/683 R; 208/58; 208/60; 208/107; 208/108
[58] Field of Search ...................... 208/58, 59, 60, 107, 208/108; 260/683 R, 672 R, 676 R

[56] References Cited

U.S. PATENT DOCUMENTS

| | | | |
|---|---|---|---|
| 1,857,814 | 5/1932 | Krauch et al. | 208/107 |
| 2,759,806 | 8/1956 | Pettyjohn et al. | 208/107 |
| 3,073,777 | 1/1963 | Oettinger | 208/107 |
| 3,148,135 | 9/1964 | Schlinger et al. | 208/107 |

FOREIGN PATENT DOCUMENTS

| | | | |
|---|---|---|---|
| 823,956 | 11/1959 | United Kingdom | 260/683 |
| 1,333,776 | 10/1973 | United Kingdom | 260/683 R |
| 1,265,415 | 3/1972 | United Kingdom | 260/683 R |

*Primary Examiner*—Brian Hearn
*Attorney, Agent, or Firm*—Bernard & Brown

[57] ABSTRACT

Production of ethylene is disclosed by a route which involves hydrocracking of a $C_3$ or higher feedstock, e.g. a gas oil, followed by ethane pyrolysis. The feedstock/hydrogen ratio is chosen to favor $C_2$ production (mainly ethane but also a small proportion of ethylene) in the hydrogenation zone and the reaction is prevented from self-quenching by supplying to the hydrocracking reaction zone hot combustion gases produced by at least partial oxidation of a fuel.

8 Claims, 4 Drawing Figures

HYDROCARBON CONVERSION PROCESS

The present invention relates to the conversion of hydrocarbons into more desirable products. More particularly it relates to the production of a $C_2$ hydrocarbon containing product by vapour phase hydrogenation of a $C_3$ or higher hydrocarbon feedstock and to the use of such a $C_2$ hydrocarbon containing product in the production of ethylene.

The destructive hydrogenation or hydrocracking of hydrocarbons is well-known. In this process aliphatic hydrocarbons undergo cracking to produce lower hydrocarbons such as propane, ethane and methane. Any alkylated aromatic hydrocarbons present undergo dealkylation at least to some extent but reaction and ring cleavage of non-alkylated aromatic compounds occur to an appreciable extent only under the most severe conditions.

In this series of reactions the reaction products have a different, higher hydrogen:carbon ratio from the starting materials, and thus the reaction involves an increase in the hydrogen:carbon ratio.

This increase is greatest for the formation of methane since this has the highest possible ratio (4:1), which can be compared with a value approaching 2:1 for a high molecular weight paraffin. In the destructive hydrogenation of a hydrocarbon feedstock most of the overall heat of reaction is supplied by methane formation whereas the formation of higher hydrocarbon products such as ethane contributes relatively little to this. The nature of the products can be varied to some extent by altering the proportions of feedstock and hydrogen but in order to obtain a self-sustaining reaction a certain minimum ratio of hydrogen to hydrocarbon feedstock must be supplied to the reaction zone, the exact proportion of hydrogen depending on the nature of the feedstock. If too little hydrogen is supplied not enough methane is produced and the reaction quenches itself. Conventionally this process is operated with the aim of producing a product rich in methane and so sufficient hydrogen is provided to maximise formation of methane.

Ethylene is produced on a large scale by steam cracking of hydrocarbon feedstocks. One method uses naphtha as a starting material and as a fuel in the process but the yields of ethylene may be only in the region of 20–25% based on the naphtha consumed and the by-product "cracker gasoline" is a complex mixture of products which is difficult to separate. Higher average molecular weight hydrocarbon feedstocks can be used but the ethylene yields are lower.

Another method of producing ethylene uses ethane as a starting material. Pyrolysis of ethane, usually in the presence of steam, gives a good yield of ethylene but ethane is not usually a readily available feedstock. There have therefore been proposals to convert hydrocarbon feedstocks such as naphtha to ethane for subsequent conversion to ethylene. Such processes involve destructive hydrogenation of the feedstock and are described for example in British Patent Specifications Nos. 1,265,415 and 1,333,776. Recommended conditions for such processes include a high hydrocarbon to hydrogen ratio and temperatures of from 600° to 750° C, preferably 650° C to 725° C. However, since this reaction is self-sustaining only if a sufficient proportion of methane is produced, these processes involve conversion of a considerable proportion of the hydrogen and feedstock introduced into the reaction zone to methane rather than to ethane. Although petroleum distillate, crude petroleum and heavy oils are said to be suitable feedstocks for the process described in British Patent Specification No. 1,265,415, the process is in practice limited to naphtha feedstocks since with heavier feedstocks the yield of ethylene is reduced, the amount of carbon deposited as soot is increased and the hydrogen requirement is increased, making the process commercially unattractive for feedstocks heavier than naphtha.

Since it is relatively expensive to produce hydrogen, both in terms of the capital cost of the plant and in terms of running costs, it would be desirable to reduce the amount of hydrogen that needs to be introduced into the reaction zone. It would also be desirable to increase the proportions of ethylene and ethane produced from a given quantity of feedstock.

The invention accordingly seeks to provide a process for destructive hydrogenation of a hydrocarbon feedstock which results in a commercially attractive yield of $C_2$ hydrocarbons whilst reducing the methane content of the product and reducing the proportion of hydrogen supplied to the reaction zone that is converted to methane. The invention also seeks to provide an improved process for producing ethylene from a hydrocarbon feedstock by destructive hydrogenation thereof followed by thermal cracking of the ethane thus produced.

According to one aspect of the present invention a process for the production of $C_2$ hydrocarbons by destructive hydrogenation of a feedstock containing $C_3$ and/or one or more higher hydrocarbons comprises supplying the feedstock to a vapour phase hydrogenation zone together with hydrogen or a hydrogenating gas in a proportion favouring formation of $C_2$ hydrocarbons and maintaining the temperature in the hydrogenation zone above the threshold temperature for the reaction by supplying thereto hot combustion gases resulting from oxidation or partial oxidation of a fuel with an oxygen-containing gas.

In this way the destructive hydrogenation reaction, which would otherwise be self-quenching at the feedstock/hydrogen ratio used in the process of the invention, is prevented from self-quenching by supplying heat thereto with the aid of the hot products of combustion.

In another aspect of this present invention a process for producing ethylene comprises passing a feedstock containing $C_3$ and/or one or more higher hydrocarbons to a hydrogenation reaction zone together with hydrogen or a hydrogenating gas in a ratio favouring formation of $C_2$ hydrocarbons while maintaining the temperature in the hydrogenation zone above the threshold temperature for the hydrogenation reaction by supplying thereto hot combustion gases resulting from at least partial oxidation of a fuel with an oxygen-containing gas, recovering ethane from the resulting reaction mixture, passing the ethane through a pyrolysis zone to generate ethylene, and separating the ethylene produced. Preferably unreacted hydrogen from the hydrogenation zone and hydrogen recovered from the ethane pyrolysis zone are recycled to the hydrogenation zone. Ethane pyrolysis may be effected in the presence of steam in a tubular externally heated reactor or in an internally heated reactor, such internally heated reactor being supplied with oxygen for combustion or partial combusion of part of the feed to generate the necessary high temperature.

The destructive hydrogenation or hydrocracking reaction may be effected catalytically in the presence of a solid catalyst which is preferably in granular or pellet form. Such a catalyst may be in the form of a fixed bed or in the form of a fluidized bed. Typical catalysts include but are not limited to nickel molybdate, cobalt molybdate and the like. Thus a typical procedure involves effecting destructive hydrogenation (hydrocracking) in the presence of a cobalt molybdate catalyst (which may optionally contain tungsten). However it will usually be preferred to effect the destructive hydrogenation (hydrocracking) reaction non-catalytically. If desired this reaction can be effected in a fluidised bed of particles or granules of an inert (non-catalytic) material, such as carbon, silica, α-alumina, zirconia, thoria or the like.

The feedstock can be any convenient gaseous or liquid hydrocarbon-containing feedstock. However, if a feedstock is to be used which contains appreciable proportions of an olefin or olefins, for example pyrolysis gasoline, it is preferred to submit this to a preliminary hydrogenation step to transform it to a saturated material in order to avoid difficulties arising from deposition of carbon in any feedstock preheater.

Typical feedstocks for use in the process of this invention include propane, propylene, n- and iso-butane, butene-1, butene-2, pentane, pentene-1, pentene-2, n-hexane, hexene-1, hexene-2, commercial "hexane", "heptane", isoctane, decane, dodecane, dodecene-1, cyclohexane, decalin, tetralin, butadiene, methyl acetylene, styrene, ethyl benzene, petroleum distillates such as naphthas, kerosene, gasoline, heating oils, gas oils and vacuum distillates, coal tar distillates, crude petroleums having, for example, an API gravity above about 20, pyrolysis gasoline from a conventional olefin plant, and mixtures of two or more thereof.

The fuel used to generate the hot combustion gases can be any convenient fuel and is preferably a carbonaceous fuel. Thus the fuel may be the same as the feedstock. It may be, for example, an alcohol such as methanol or ethanol, a solid fuel such as pulverised coal, natural gas, carbon monoxide, coal gas, water gas, methane, aromatic distillates, polycyclic aromatic products of the hydrocracking reaction, or any of the materials listed above as suitable feedstocks.

The threshold temperature for the reaction is the minimum temperature at which the hydrogenation reactions are thermally self-sustaining for the chosen feedstock/hydrogen (or hydrogenating gas) ratio in the presence of added hot combustion gases and will depend to some extent on the type and composition of the feedstock. The threshold temperature will also depend on the ratio of the reactants (the feedstock/hydrogen ratio), on the reactor design and on the amount of preheat imparted to the incoming reactants. It will usually be in the region of about 700° C but it may be as low as about 650° C or as high as about 750° C for particular feedstocks and feedstock/hydrogen ratios. The process can be operated at any temperature above the threshold temperature up to about 900° C or higher. Generally the reaction in the hydrogenation zone is conducted at a temperature at least about 20° C above the threshold temperature. Since formation of $C_2$ hydrocarbons is at least to some extent temperature-dependent, higher $C_2$ yields generally being obtainable at lower temperatures, it is preferred to operate the hydrocracking process of this invention at temperatures as close to the threshold temperature as is practicable. Thus the process is usually operated to best advantage at temperatures between about 20° C and about 50° C above the threshold temperature, e.g. within the range of from about 20° C to about 30° C above the threshold temperature for the reaction. The lower the temperature, however, the longer the residence time of the reactants in the hydrocracking zone must be. Conversely, the higher the temperature of the hydrocracking zone the shorter must be the residence time. Generally speaking residence times in the hydrocracking zone of from about 4 to about 40 seconds, for example about 5 to about 15 seconds are preferred.

The rate of supply of hot combustion gases to the hydrogenation zone will be sufficient to maintain the temperature in the hydrogenation zone above the threshold temperature for the reaction. The combustion gases are generated externally to the hydrocracking reaction zone and injected, preferably at high velocity, into the latter separately from the feedstock feed point. The temperature of the combustion gases will exceed the threshold temperature by a considerable margin. Thus they may have a temperature of about 1000° C or more, e.g. about 1200° C to about 1500° C or higher. The combustion gases can be premixed with the hydrogen or hydrogenating gas, or introduced separately from the hydrogen or hydrogenating gas feed point. Such combustion gases may have for example, a temperature of about 1000° C up to about 1400° C or more, e.g. about 1250° C to about 1350° C. In one arrangement the combustion gases are generated in a reactor of a type similar to a gas recycle hydrogenator connected to the hydrocracking reaction vessel or forming a part thereof.

If fuel is a carbonaceous fuel and if the combustion of the fuel is complete, i.e. if the fuel is burnt so as to yield wholly carbon dioxide and water and possibly also minor amounts of other combustion products, then generation of the combustion gases must be effected externally to the hydrocracking reaction zone. Partial combustion leads mainly to formation of carbon monoxide rather than carbon dioxide and is preferred for reasons which will appear below. It will usually be preferred to use an oxygen-rich gas for the production of the hot combustion gases. Thus essentially pure oxygen will, in many cases, be preferred as the oxidation medium for the combustion since this avoids introducing inert gases such as nitrogen into the reaction zone. If air is used the nitrogen present in air may be an unwanted diluent which is difficult and expensive to separate from methane. Other oxygen-rich gases that can be used include oxygen/carbon dioxide mixtures preferably containing at least about 80% by volume of oxygen.

The hydrogen or hydrogenating (hydrogen-containing) gas can be formed in any convenient manner, e.g. by electrolysis of aqueous solutions, by catalytic steam reforming of methane and/or other hydrocarbons, or by the shift reaction of carbon monoxide, or derived from oil refining operations.

The feedstock and the hydrogen or hydrogenating gas are preferably preheated either separately or premixed and then the preheated feedstock and hydrogen or hydrogenating gas are fed to the reaction zone. The feedstock can thus be supplied to the hydrogenation zone either in vapour form or in liquid form, e.g. in the form of atomised droplets, depending on the nature of the feedstock and the temperature to which it is preheated. Preheating may be accomplished, for example, by indirect heat exchange with the hot reaction products from the hydrocracking reaction zone.

In the hydrogenation zone the ratio of hydrogen or hydrogenating gas to feedstock is chosen so as to favour the formation of $C_2$ hydrocarbons, at the expense of formation of methane. However it is not possible to avoid formation of methane altogether. The ratio is dependent on the nature of the feedstock but in general a high feedstock to hydrogen ratio is employed. Thus for the hydrogenation of crude petroleum the ratio of feedstock to hydrogen in the hydrogenating gas is generally from about 3 to about 10 gallons of petroleum per 1000 scf (standard cubic feet) of hydrogen and preferably above about 6 gallons per 1000 scf. The use of high hydrocarbon to gas ratios tends to favour a high proportion of aromatic hydrocarbons in the reaction-product mixture. Thus for a typical gas oil a ratio of feedstock to hydrogen greater than about 3 gallons per 1000 scf is preferably used, for example around 4.25 gallons per 1000 scf of hydrogen. However, higher feedstock to hydrogen ratios can also be used, e.g., up to about 27 gallons per 1000 scf but these ratios tend to lead to a smaller overall yield of ethane and a higher yield of aromatics. Of course if partial combustion is effected in the hydrogenation zone by introduction of the oxygen-containing gas into the hydrogenation zone then the hydrocarbon/hydrogen ratio must be correspondingly altered to allow for combustion of some of the feedstock and/or of the hydrogen.

In the destruction hydrogenation of a hydrocarbon feedstock the nature and composition of the product stream are influenced by the feedstock/hydrogen ratio as well as by the nature of the feedstock. At low feedstock/hydrogen ratios, e.g. about 0.5 gallons per 1000 scf of hydrogen for a typical gas oil, the product stream will contain large amounts of free hydrogen and various hydrocarbon products. The major hydrocarbon product will be methane together with lesser amounts of ethane, ethylene, propylene, propane, traces of $C_4$ and higher aliphatic hydrocarbons, and aromatic hydrocarbons such as benzene, toluene, xylenes (o-, m- and p-), diphenyl, naphthalene and polycyclic aromatic hydrocarbons. An increase in the feedstock/hydrogen ratio initially reduces the excess hydrogen content of the product stream without materially affecting the conversion of the hydrocarbon feedstock to methane and the other listed products. As the feedstock/hydrogen ratio is further increased, the percentage conversion to methane falls with a corresponding increase in production of $C_2$ hydrocarbons. This increase in $C_2$ hydrocarbon production is, however, accompanied by a fall in the amount of heat released by the reaction since less of the product is converted to methane, the heat release being greater for methane formation than for $C_2$ and higher hydrocarbon formation. Further increase in the feedstock/hydrogen ratio leads to an increase in the production of aromatic products (e.g. benzene, toluene, xylenes, naphthalene and aromatic polycyclic hydrocarbons) and to the formation of carbon and tarry materials. Formation of carbon and tarry materials tends to occur in particular if the partial pressure of hydrogen in the exit gases falls too low. If the feedstock/hydrogen ratio is increased too much in the process described in British Patent Specifications Nos. 1,265,415 and 1,333,776 the reaction eventually becomes self-quenching as already mentioned. For some feedstocks (e.g. gas oils) the hydrocracking reaction may be self-sustaining (once initiated) only at feedstock/hydrogen ratios close to the ratio at which methane formation is maximised. For others (e.g. naphtha) some improvement in yield of $C_2$ hydrocarbons may be achieved by increasing the feedstock/hydrogen ratio without self-quenching occurring.

By using the hydrocracking process of the present invention, however, the range of feedstocks that can be utilised for economically attractive production of $C_2$ hydrocarbons by the hydrocracking route is greatly extended. Thus gas oils and similar feedstocks are made available for commercial production of ehtylene by this route.

Generally speaking the feedstock/hydrogen ratio to be used in the hydrocracking process of the invention is greater than that required to maximise methane formation.

Although the feedstock/hydrogen ratio to be used in the hydrocracking process of the present invention can be found by a process of trial and error, it is possible to calculate this ratio if the characteristics of the reactor, the operating temperature and the properties of the feedstock are known. For such calculations, as will be well-known to the man skilled in the art, the required characteristics of the feedstock include the C:H (carbon:hydrogen) ratio, its P:N:A (paraffins:naphthenes:aromatics) ratio, as well as its ASTM boiling ranges (e.g. the initial boiling point, and the 10%, 20% and 50% boiling points, that is to say the boiling point of the residue after distillation of 10%, 20% and 50% by weight respectively of a sample of the feedstock). Other valuable information for the calculations includes the Conradson carbon number (which gives an indication of the percentage of coke formed upon distillation of a sample of the feedstock) and the sulphur and nitrogen contents of the feedstock.

There will be a body of experimental data available to the man skilled in the art relating to the chosen design of reactor, from which he will be able to deduce survival parameters for each of the main components of the product stream (e.g. methane, ethane, propylene, benzene, toluene, xylenes, diphenyl, naphthalene, and anthracene). From these data, knowing the residence time in the reactor etc., he can deduce the likely exit gas composition from the reactor. Using this exit gas composition he can then arrive at a carbon balance for the rector from which the amount of hydrogen required can be readily calculated. He can go on to do an enthalpy balance calculation using published thermodynamic data and hence deduce a thermal balance from whch the quantity and temperature of hot combustion gases required to sustain the hydrocracking process of the invention can be calculated.

The reaction vessel in which the destructive hydrogenation of hydrocracking reaction is carried out can be of any suitable type, for example, a plug flow reactor, a fludizied bed reactor, an internal recycle reactor in which the reaction mixture is recirculated several times through the reaction zone, or any combination of such vessels. The residence time in the reaction vessel will usually be from about 2 seconds upwards, e.g. from about 4 to about 40 seconds, but is preferably from about 5 to about 15 seconds.

If the feedstock has a low sulphur content it will usually be preferred to introduce deliberately a small amount of sulphur, e.g. in the form of $CS_2$, into the hydrogenation zone in order to ensure that all the metallic surfaces are sulphided thereby inhibiting carbon desposition within the reactor vessel. The amount of CS$_2$ added can be varied as required to ensure that a small but detectable quantity of sulphur is present in the exit gases from the hydrogenation zone.

The hydrocracking reaction is generally carried out at a pressure above about 3 atmospheres absolute and preferably at a pressure in the range of from about 3 to about 70 atmospheres absolute. Higher pressures can be used if desired but there is little advantage in operating at pressures in excess of about 70 atmospheres absolute. The product from the hydrocracking reaction is preferably treated for recovery of ethane by conventional methods. Thus for example the reaction products can be fed to a cooler in which any readily condensible normally liquid or solid products are condensed out from the product stream whereas the gaseous products pass on for further treatment. Such readily condensible products typically comprise aromatic liquid hydrocarbons and polycyclic aromatic products. The cooler can be followed by a washing stage in which an oil is used to wash the last traces of aromatic liquid hydrocarbon products out of the gaseous products, the oil being passed to a stripper for recovery of the aromatic liquid hydrocarbon products and recycled to the washing stage. The hydrocarbon condensate will usually consist essentially of a mixture of aromatic liquid hydrocarbons, such as benzene, toluene and xylene, together with some polycyclic aromatic material, and will contain little or no aliphatic hydrocarbons. The liquid aromatic hydrocarbons can be separated from the polycyclic components without difficulty by distillation. So-called "nitration grade" benzene and toluene can be produced in this way as well as a mixture of xylenes. In comparison, the cracker gasoline obtained from a conventional steam reforming cracker is a complex mixture of aliphatic and aromatic hydrocarbons which cannot be separated readily by distillation. It is thus an advantage of the process that the liquid product can be readily purified. The naphthalene and other polycyclic aromatic products can be used as a fuel, for example as the carbonaceous fuel for generation of the hot combustion gases or for heating the ethane pyrolysis reactor tubes or as a source of carbon monoxide produced by partial combustion for use in a subsequent CO shift reaction to provide hydrogen for the process.

As already mentioned it is preferred to use partial oxidation of a carbonaceous fuel to produce the hot combustion gases used to maintain the temperature in the hydrogenation zone above the threshold temperature for the reaction. The reason for this is that the carbon monoxide thus produced can be submitted to a CO shift reaction downstream from the hydrogenation zone in order to generate hydrogen for recycle to the hydrogenation zone.

The combustion of the fuel, whether partial or complete, is preferably effected with an oxygen-rich gas, that is to say one containing at least about 80% by volume oxygen. Essentially pure oxygen is preferably used as the oxygen-contining gas since this does not introduce any undesired interfering products into the reaction mixture from the hydrogenation zone. Thus the oxygen-containing gas preferably comprises at least about 95% up to about 99% or more by volume of oxygen. The presence of nitrogen will usually be undesirable since it is preferred to recycle unreacted hydrogen to the hydrogenation zone and, unless nitrogen were removed, it would build up in the gas recycle stream. Removal of nitrogen would involve an extra cryogenic separation stage or stages thus adding unnecessarily to the capital costs and running expenses. For this reason it will usually be preferred to operate the process of the present invention with an oxygen-rich gas that is essentially nitrogen-free.

The gas stream from the hydrogenation zone, after removal of the aromatic hydrocarbon products and any water present will usually consist of methane, ethane, a small proportion of ethylene, minor amounts of propylene and other gaseous hydrocarbons, carbon monoxide and/or dioxide and unreacted hydrogen. This gaseous product mixture can be further processed in a number of ways.

The aromatic-depleted gas stream from the hydrogenation zone can be passed without further treatment to a pyrolysis zone for conversion of ethane to ethylene, steam being injected into the pyrolysis zone or into the gas stream upstream of the pyrolysis zone. The reaction mixture from the pyrolysis zone can then be washed with alkali to remove acid gases such as carbon dioxide and hydrogen sulphide compressed and separated by cryogenic techniques. In one form of plant the pryolysis product mixture is passed to a first cryogenic separation stage in which the lighter, lower boiling point gases consisting of hydrogen, carbon monoxide and methane are taken off as an overhead stream whilst the ethylene, unreacted ethane and C$_3$ and higher hydrocarbons appear as a bottom product. The overhead stream is then submitted to a further cryogenic separation stage to separate most of the methane whilst the hydrogen, carbon monoxide and some of the methane are recycled to the hydrogenation zone via a catalytic steam reformer and a CO shift reaction zone followed by CO$_2$ removal. The bottom product is sent to a de-ethaniser where C$_3$ and higher products are removed as a bottom product while ethane and ethylene are removed in the overhead product line. After separation of the ethylene in a subsequent step unreacted ethane is recycled to the pyrolysis zone.

In an alternative arrangement the reaction mixture from the hydrogenation zone is first washed with alkali to remove acid gases and is then at least partially separated into its components and an ethane-contining fraction is passed to the pyrolysis zone. In one form of plant the reaction product from the hydrogenation zone, after aromatics removal and alkali washing, is passed to a cryogenic separation stage in which the C$_2$ and highr hydrocarbons are separated from the lighter gases (H$_2$, CO and CH$_4$) and passed to an ethane pryolysis zone, steam being injected into or upstream of this pyrolysis zone. The product from the ethane pyrolysis zone is submitted to a second cryogenic separation zone to separate hydrogen and methane from the C$_2$ and higher hydrocarbon products which are themselves sent to a de-ethaniser unit. C$_2$ hydrocarbons are taken off as an overhead stream whilst C$_3$ and higher hdyrocarbons are taken off as a bottom product. After separation of ethylene in a subsequent step unreacted ethane is recycled to the pyrolysis zone. The lighter gases from the hydrogenation zone and the hydrogen/methane mixture from the second cryogenic separation zone are then combined and passed to a de-methaniser, in which most of the methane is recovered, whilst the hydrogen and carbon monoxide together with some of the methane are recycled via a catalytic steam reformer and a CO shift reaction stage followed by CO$_2$ removal to the hydrogenation zone. In this way further hydrogen is provided for the process from the carbon monoxide produced by partial oxidation of the carbonaceous fuel.

In a modification of this form of plant the $C_2$ and higher hydrocarbons are separated from the methane and lighter gases in the reaction product from the hydrogenation zone by solvent extraction in an oil. The oil is passed to a stripping stage from which the adsorbed hydrocarbons are recovered and further processed as described in the preceding paragraph while the oil is recycled to the extraction stage.

In another form of plant involving at least partial separation of the reaction mixture from the hydrogenation zone into its components, the gaseous hydrocarbon products after removal of aromatic products and carbon dioxide are separated cryogenically from th lighter gases ($H_2$ and CO) in a primary separation stage. The methane is separated in a de-methaniser. The $C_2$ and higher hydrocarbons are then fed to a de-ethaniser and thence to an ethylene/ethane splitter. The ethane and heavier hydrocarbons (traces of propane, propylene, butanes and butylenes) can then be mixed with steam and fed to an ethane pyrolysis unit. The cracked gas from the ethane pyrolysis unit can be cooled, compressed, washed with an alkali such as caustic soda to remove traces of $H_2S$ and $CO_2$ and dried before return to the primary separation stage. Ethane and ethylene are separated from the stream from the pyrolysis unit and are returned to the ethane/ethylene splitter via the de-ethaniser, whilst hydrogen formed in the pyrolysis of the ethane is recycled via the steam reformer and CO shift reaction stage to the hydrocracking zone.

An alternative form of "light ends" fractionation system for treatment of the product from the hydrogenation zone is that customarily employed with a conventional steam pyrolysis unit for cracking naphtha, ethane or propane. Such a fractionation system is described for example, in the aforementioned British Patent Specification No. 1,333,776 the disclosure of which is herein incorporated by by reference.

Further details of ethane pyrolysis can be found in "Ethylene and its Industrial Derivatives" edited by S. A. Miller, published by Ernest Benn Limited, London (1969), especially at Chapter 3 pages 103 to 149 and in the article entitled "Ethylene" which appears at pages 499 to 523 of Volume 8 of "Kirk-Othmer Encyclopedia of Chemical Technology" Second Edition published by Interscience Publishers (1965), the disclosures of both of which sources of reference are herein incorporated by reference.

Methane produced in the hydrogenation zone and recovered, for example, as outlined above can be used as the carbonaceous fuel for generation of the hot combustion gases or can be steam reformed to produce hydrogen for the process or can be used elsewhere as a fuel. Usually the methane will be used for a combination of these purposes.

Pyrolysis of the ethane is preferably effected at a temperature of from about 700° C to about 950° C, more preferably about 750° C to about 900° C. The pressure in the pyrolysis zone is preferably in the range of from 1 to 5 atmospheres absolute. As already mentioned steam may be admixed with the ethane before or during passage through the pyrolysis zone, for example, in an amount of from about 0.1 to about 2 moles or more, preferably about 0.3 to about 1 mole of steam per mole of ethane.

If the pyrolysis is effected in an externally fired tubular reactor this can be heated at least in part by combustion of the naphthalene and other aromatic polycyclic products of the hydrocracking reaction or by combustion of methane produced by the hydrocracking reaction.

The production of ethylene by this invention can be carried out in parallel with a conventional olefin plant operating, for example, on the same feedstock. Since the production of ethylene by the process of the present invention results in the production of only small proportions of propylene compared with ethylene, the parallel operation permits the output of $C_2$ and $C_3$ olefins from the combined plant to be balanced according to market demand by varying the proportions of feedstock fed to the two plants so as to give a desired ratio of ethylene to propylene from a given feedstock.

It is possible by the process of the present invention to convert to ethylene upwards of 30% by weight of a feedstock such as a gas oil boiling at a temperature of 240° to 324° C whilst reducing the amount of methane produced to less than 35% by weight. Besides producing more of the more desirable product ethylene at the expense of methane compared with conventional operation of a gas recycle hydrogenator followed by ethane pyrolysis, the process of this invention has the added advantage that its hydrogen requirements for a given feedstock are reduced, since less hydrogen is needed for conversion to methane. Thus capital investment in hydrogenating gas-producing plant and the running costs associated with hydrogen production are reduced compared with operation of a conventional gas recycle hydrogenator/ethane pyrolysis plant such as is described in British Patent Specifications Nos. 1,265,415 and 1,333,776.

An example of a process carried out in accordance with the present invention is illustrated by reference to FIG. 1 of the drawings which is a schematic flowsheet of a process employing the present invention in an ethylene production plant. In this flowsheet the various process stages are represented by interconnected closed areas. Equipment such as valves, heat exchangers and the like have been omitted for the sake of simplicity and will be provided in accordance with standard chemical engineering practice as will immediately be apparent to the man skilled in the art.

A feedstock of gas oil is fed by line 1 to a gas phase reactor represented at 25 in which destructive hydrogenation is effected. The reactor is also fed by hot gases through line 3 and by hydrogen containing gases through line 5 and hydrogenation products proceed by the outlet line 4 to heat recovery and quenching stages as well as aromatics recovery represented by the area 26. The feedstock is preheated for the reaction by passage through heat exchanger 39. Hot gases are also injected into the reactor and are derived from a generator represented at 27 to which oxygen is fed through line 2. Methane for combustion or partial combustion is fed to generator 27 through line 6. Reactor 25 and generator 27 can be of any suitable design, e.g. plug flow reactors or fluidized bed reactors, but are preferably constructed as recycle reactors of the type described in British Patent Specification Nos. 1,031,717 and 1,074,932.

After hydrogenation light aromatic products (consisting mainly of benzene, toluene and xylenes) are recovered at stage 26 by line 7 and heavy aromatics, mainly polycyclic by-products, are removed via line 8 for use as fuel. The main product stream continues by line 17 to stage 37 for acid gas removal and drying. In stage 37 acid gases such as $CO_2$ and $H_2S$ are removed by washing with, for example, $K_2CO_3$ solution or diethanolamine solution via line 9 for further treatment if required.

Offtake 10 from stage 37 leads to a cryogenic gas separation stage 28. Light gases consisting of hydrogen and carbon monoxide with some methane are removed in line 11 and methane by line 12. Remaining product gases proceed by line 18 to an ethylene separation stage 29. The ethylene is de-ethanated in stage 29 and ethane proceeds by line 13 to the ethane cracker stage 30. The cracked gas is passed by line 19 to be cooled, compressed, washed with caustic soda to remove $H_2S$, and dried at stage 31 from which it is returned by line 14 to the gas separator 28 whereby ethane is recycled to cracker 30 by line 13 and ethylene is recovered at line 16 by the ethylene separation stage 29. De-ethaniser bottoms are recovered in line 15 and consist mainly of $C_3$ and some higher hydrocarbons.

Methane in line 12 is available as a final product, some of which is passed by line 6 to the hot gas generator 27 and some by line 20 for use as a fuel for steam reforming, with a balance of product methane remaining which can be removed via line 40 for use as a fuel elsewhere.

The light gases in line 11 are passed to a steam reforming stage 32 and to a CO shift reaction stage represented at 38 to provide a hydrogen gas stream for line 5. Carbon dioxide is also removed from the product gases and such removal is represented by line 21. Water or steam is added for reaction at stage 32 through the line 22. By-pass lines 41 and 42 permit control of the temperature of hot gases supplied through line 3 by admixture of the hot combustion gases from the hot gas generator 27 with recycle methane and/or with hydrogen containing gases from CO reaction shift stage 38.

In the arrangement illustrated in FIG. 1 a reducing gas (i.e. a mixture containing carbon monoxide and hydrogen) is produced by partial oxidation in the hot gas generator 27 and also by steam reforming of methane in the steam reformer 32. In some cases, particularly in locations where oxygen is available cheaply, it may be desirable to use partial oxidation reactions instead of, or in partial replacement of, the steam reforming reactions used in reformer 32. Thus steam reformer 32 may be replaced or supplemented by a partial oxidation plant 43 operating on oxygen (supplied by line 44) and any convenient carbonaceous fuel, e.g. methane (supplied by line 45) or polycyclic aromatics (supplied by line 46). Also steam reformer 32 can be fuelled by naphthalene and other polycyclic aromatics via line 47 instead of, or in supplement to, methane supplied via line 20. Line 48 indicates the feed line for oxidation gases from partial oxidation plant 43 to shift conversion stage 38.

COMPARATIVE EXAMPLE A

A gas recycle hydrogenator (of the type described in British Patent Specifications Nos. 1,031,717 and 1,074,932) is designed to be fed at a rate of 100 tons/day with a gas oil and at a rate of 14.894 tons/day with hydrogen. This corresponds to an oil:gas ratio of 4.251 Imperial gallons gas oil/1000 scf hydrogen. The design operating temperature is 700° C approximately. The gas oil has the following specification:

CRUDE TBP cut point (°F); 465 - 615
Approx TBP range of fraction (°F); 465 - 650
GRAVITY 37.2° API; (0.839 SG)
Sulphur % w/w; 0.93
Molecular wt; 225.96
Paraffins/naphthenes/aromatics ratio (vol %); 40-38-22
Mean Average Bpt (°F); 540

The oil which has a heat of formation at 25° C of 630 BTU/lb is supplied to the feedstock preheaters at a temperature of 25° C. The system is designed so that the product from the gas recycle hydrogenator leaves the system at a temperature of 368° C having given up sensible heat to the feedstock in the preheaters, and is analysed to have the following composition:

Component; tons/day
$CH_4$; 35.228
$C_2H_6$; 46.876
$C_2H_4$; 1.963
$C_3H_6$; 2.945
$H_2$; 6.429
$H_2S$; 0.954
$C_6$ to $C_8$ aromatics; 14.619
Polycyclic aromatics; 5.88
Total; = 114.894

Figure 2:
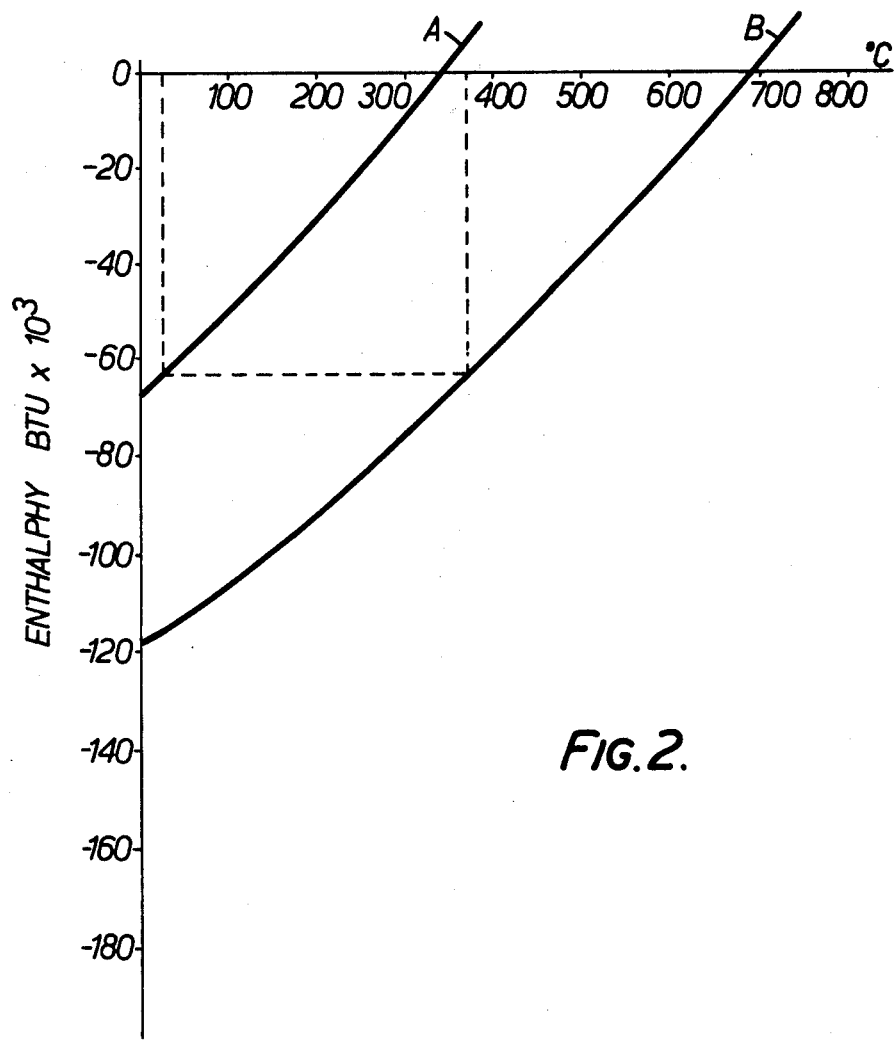

FIG. 2 shows the calculated enthalpies for the feed and product streams. With gas oil and hydrogen entering the system at 25° C and products leaving at 368° C there is no net heat loss or gain. Theoretically the reaction should just be self-sustaining but this ignores the heat losses that would occur in practice and which would result in the reaction quenching.

COMPARATIVE EXAMPLE B

The design procedure of Comparative Example A is repeated except that, whilst the throughput of gas oil remains at 100 tons/day, the throughput of hydrogen is increased to 16.354 tons/day. This corresponds to a gas oil:hydrogen ratio of 3.87 Imperial gallons gas oil/1000 scf hydrogen. The design operating temperature is 750° C approximately. The system is designed so that under these operating conditions the product from the gas recycle hydrogenator leaves the hydrogenator preheaters at a temperature of 350° C and is analysed to have the following composition:

Component; tons/day
$CH_4$; 90.232
$C_2H_6$; 7.121
$C_2H_4$; 0.8303
$C_3H_6$; 1.2456
$H_2$; 2.9841
$H_2S$; 0.9567
$C_6$ to $C_8$ aromatics; 10.2564
Polycyclic aromatics; 2.7270
Total; = 116.352

Figure 3:
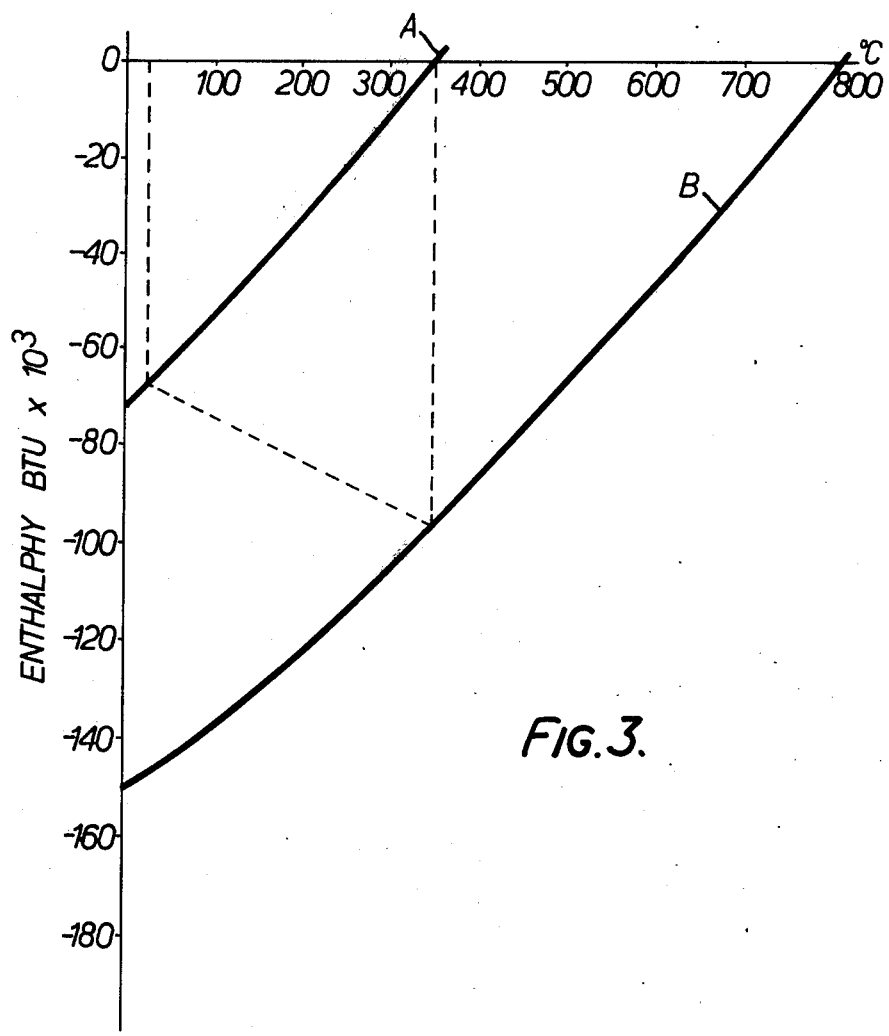

FIG. 3 shows the calculated enthalpies for the feed and product streams. With gas oil and hydrogen entering the system at 25° C and products leaving at 350° C it can be seen that a considerable amount of heat would be released. The reaction would therefore be self-sustaining but the yield of $C_2$ products has dropped from 48.839 tons/day to 7.9513 tons/day. The proportion of methane has risen from 35.228 tons/day to 90.232 tons/day.

EXAMPLE C

The gas recycle hydrogenator of Comparative Examples A and B is provided for this Example with a hot gas generator connected as illustrated in FIG. 1. The hot gas generator 27 is designed to be fed with methane and 5.984 tons/day of oxygen. The operating temperature of the gas recycle hydrogenator 25 is 700° C and the hydrogenator 25 is fed with the hot combustion gases resulting from the partial oxidation of methane in the hot gas generator 27 (i.e. a mixture of carbon monoxide, carbon dioxide, hydrogen and water vapour). The hot gas generator 27 is fed with a minimum of 2 tons/day methane and the reaction temperature in the hydrogenator 25 is controlled in part by recycling excess methane via line 6 to the hot gas generator 27, i.e., by diverting methane from line 40 through line 6.

Figure 4:
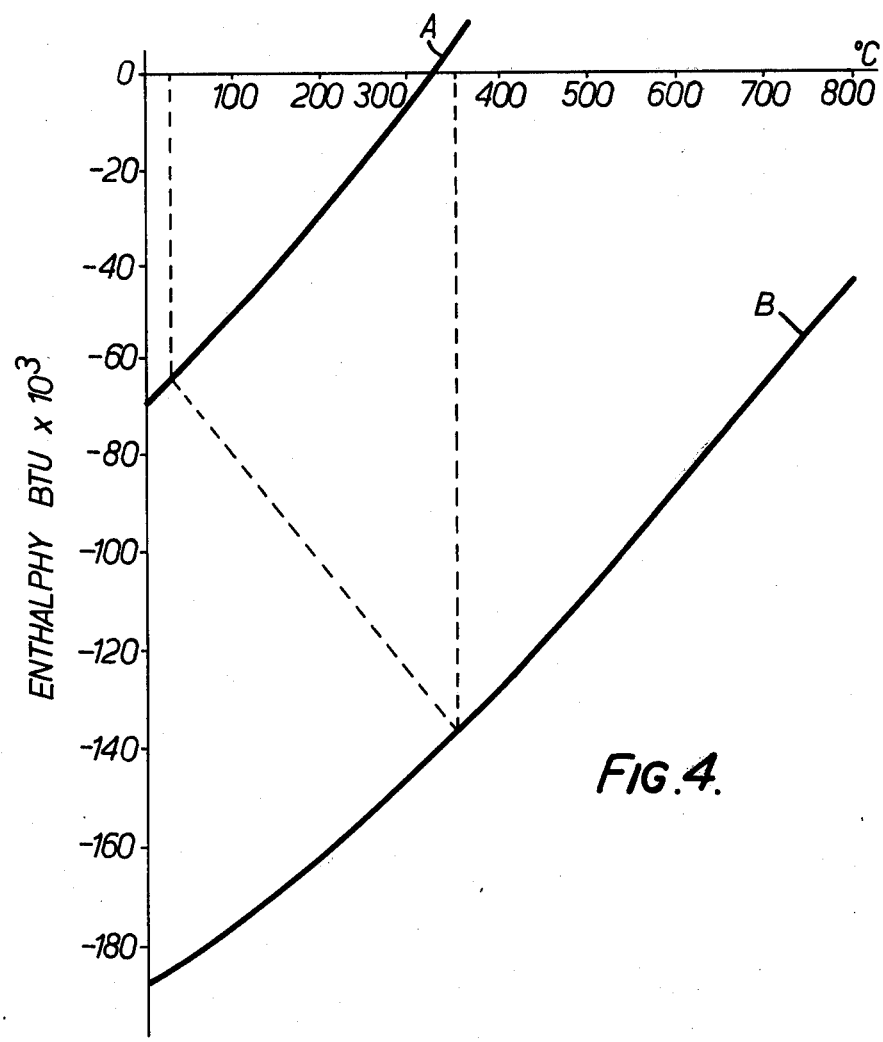

The gas oil feed rate is again 100 tons/day and the hydrogen requirement is now 14.894 tons/day. As in Comparative Example A the gas oil/hydrogen ratio is 4.251 Imperial gallons gas oil/1000 scf hydrogen. The system is designed so that the product from the hydrogenator leaves the hydrogenator preheaters at 350° C and has the same composition (ignoring excess recycled methane), as that of Comparative Example A. The calculated enthalpies of the reactants and products are shown in FIG. 4. With gas oil, hydrogen, oxygen and methane entering the system at 25° C and reaction products leaving at 350° C, the calculations show that a satisfactory thermal balance would be achieved.

As already mentioned, the temperature of the hot gases is controlled by varying the rate of recycle of methane via line 6 to the hot gas generator 27. A further method of control is by variation of the oxygen feed rate via line 2 to the hot gas generator 27. In this way compensation can be made for variations in the feedstock and in the prevailing climatic conditions, as well as in the effectiveness of the thermal insulation and of the regenerative heat equipment.

Compared with Comparative Example B Example C shows the advantage that the $C_2$ yield from 100 tons/day of gas oil is raised from 7.953 tons/day $C_2$ products to 48.839 tons/day, while the hydrogen requirement is reduced from 16.354 tons/day to 14.894 tons/day, a reduction of 1.46 tons/day or almost 9%. In Example C, the carbon monoxide supplied as a result of partial combustion in the hot gas generator is a potential source of hydrogen for treatment in the CO shift section of zone 38 of FIG. 1. The reducing gases (i.e. the carbon monoxide and hydrogen) produced by the hot gas generator in Example C, after a CO shift reaction, are equivalent to about 2% of the hydrogen requirement for the hydrogenator. This results in an economy in the methane requirement for the steam reformer 32. Since CO is a component of the product stream from the hydrogenator this means that, because the methane requirement of the steam reformer 32 is smaller for the same gas oil throughput, it can be built at a lower capital cost.

Compared with the processes of British Patent Specifications Nos. 1,265,415 and 1,333,776 the process of the present invention has the advantage that it produces less methane and requires less hydrogen for hydrocracking a given quantity of a feedstock whilst producing considerably more of the valuable $C_2$ products and a useful proportion of light aromatics. Thus, as shown by Example C, the process of the invention can yield of the order of 49 tons of $C_2$ products (ethane + ethylene) from 100 tons of gas oil in addition to 14.6 tons of light aromatics (benzene + toluene + xylenes + ethyl benzene); the methane yield is only 35 tons from this quantity of gas oil. If the hydrogenator is run without injection of the hot combustion gases the yield of $C_2$ products is less than 8 tons and the methane yield is up to 90 tons.

What is claimed is:

1. A process for producing ethylene which comprises:

(a) feeding a carbonaceous fuel and an oxygen-containing gas to a combustion zone;
    (b) maintaining the fuel to oxygen ratio in the combustion zone at a ratio such that the fuel is partially combusted to form a hot gaseous carbon monoxide-containing combustion product gas;
    (c) Supplying hydrogen and a hydrocarbon feedstock at a predetermined ratio to a non-catalytic vapour phase hydrogenation zone, the hydrocarbon feedstock being selected from $C_3$ and higher hydrocarbons and mixtures thereof, and the predetermined ratio being chosen to favour formation of ethylene and ethane in the hydrogenation zone at the expense of formation of methane, and the predetermined ratio further being such that the hydrogenation reaction is liable to self-quenching;
    (d) maintaining the temperature in the hydrogenation zone above the threshold temperature for the hydrogenation reaction at the chosen predetermined hydrogen to hydrocarbon feedstock ratio by admitting thereto hot combustion product gas from step (b) thereby preventing the hydrogenation reaction from self-quenching;
    (e) recovering from the hydrogenation zone a reaction product stream;
    (f) separating an ethane fraction from the reaction product stream;
    (g) separating a light gas fraction containing carbon monoxide from the reaction product stream;
    (h) passing ethane fraction from step (f) to an ethane pyrolysis zone maintained under ethane pyrolysis condition to convert ethane to ethylene;
    (i) recovering ethylene from step (h);
    (j) submitting carbon monoxide of the light gas fraction from step (g) to a water gas shift conversion step in a shift conversion zone for conversion of carbon monoxide to carbon dioxide and concurrent generation of hydrogen;
    (k) recovering from this shift conversion zone a shifted gas product containing carbon dioxide and hydrogen;
    (l) removing carbon dioxide from resulting shifted gas product; and
    (m) recycling resulting hydrogen containing gas to the noncatalytic vapour phase hydrogenation zone.

2. A process according to claim 1, in which the temperature in the hydrogenation zone is maintained at a temperature of from about 650° C. to about 750° C. and at a pressure of from about 3 to about 70 atmospheres absolute.

3. A process according to claim 1, in which the temperature in the hydrogenation zone is maintained in the range of from about 20° C. to about 50° C. above the threshold temperature for the reaction.

4. A process according to claim 1, in which the feedstock is a gas oil.

5. A process according to claim 1, in which the carbonaceous fuel comprises polycyclic aromatic products recovered from the reaction product stream of step (e).

6. A process according to claim 1, in which the light gas fraction resulting from step (g) contains hydrogen, carbon monoxide and methane and is passed together with steam to a steam reforming zone for reforming of methane therein to produce further carbon monoxide and hydrogen prior to passage to the shift conversion zone of step (j).

7. A process according to claim 1, in which hydrogen produced in the ethane pyrolysis zone of step (h) is recycled to the hydrogenation zone.

8. A process for the production of ethylene which comprises:
   (a) feeding hydrogen and a hydrocarbon feedstock comprising at least one $C_3$ or higher hydrocarbon to a vapour phase non-catalytic destructive hydrogenation zone;
   (b) maintaining the hydrogen to hydrocarbon feedstock ratio at a value favouring formation of ethane and ethylene whilst reducing the formation of methane, said value being such that the destructive hydrogenation reaction is liable to self-quenching;
   (c) feeding a carbonaceous fuel and an oxygen-containing gas to a combustion zone;
   (d) maintaining the fuel to oxygen ratio at a value such that the fuel is partially combusted in the combustion zone;
   (e) supplying resulting hot carbon monoxide-containing combustion products from the combustion zone to the hydrogenation zone, thereby to maintain the temperature of the hydrogenation zone above the threshold temperature for the destructive hydrogenation reaction at the chosen hydrogen to hydrocarbon feedstock ratio and to prevent the destructive hydrogenation reaction from self-quenching;
   (f) recovering from the hydrogenation zone a gaseous product stream;
   (g) recovering an ethane fraction from the gaseous product stream;
   (h) passing resulting ethane fraction to an ethane pyrolysis zone maintained under ethane pyrolysis conditions, thereby to pyrolyse ethane to ethylene and hydrogen;
   (i) recycling hydrogen resulting from step (h) to the hydrogenation zone;
   (j) recovering ethylene resulting from step (h);
   (k) recovering from the gaseous product stream resulting from step (f) a light gas fraction containing carbon monoxide, hydrogen and methane;
   (l) passing light gas fraction from step (k) to a steam reforming zone together with steam for reforming of methane therein to generate further carbon monoxide and further hydrogen;
   (m) recovering from the steam reforming zone a reformed light gas fraction;
   (n) submitting reformed light gas fraction from step (m) to a water gas shift conversion step in a shift conversion zone for conversion of carbon monoxide to carbon dioxide and generation of further hydrogen;
   (o) recovering carbon dioxide formed in step (n); and
   (p) recycling further hydrogen from steps (l) and (n) to the hydrogenation zone.

* * * * *